United States Patent [19]

Shibuya et al.

[11] 4,066,781
[45] Jan. 3, 1978

[54] MITICIDAL METHOD

[75] Inventors: Hajime Shibuya, Komae; Shiroh Shirato, Tokyo, both of Japan

[73] Assignee: Kaken Chemical Co., Ltd., Tokyo, Japan

[21] Appl. No.: 763,234

[22] Filed: Jan. 27, 1977

[51] Int. Cl.$^2$ .................. A01N 9/28; A61K 31/35
[52] U.S. Cl. ............................................... 424/283
[58] Field of Search ........................................ 424/283

[56] References Cited

U.S. PATENT DOCUMENTS 3,857,948  12/1974  Tanaka et al. .................. 424/283

FOREIGN PATENT DOCUMENTS 51-57820  5/1976  Japan .............................. 424/283

Primary Examiner—Jerome D. Goldberg
Attorney, Agent, or Firm—Oblon, Fisher, Spivak, McClelland & Maier

[57] ABSTRACT

Salinomycin is applied as an active ingredient of a miticidal composition to mites.

3 Claims, No Drawings

MITICIDAL METHOD

BACKGROUND OF THE INVENTION

1. Field of the Invention:

The present invention relates to a miticidal method for inhibiting development of mites.

2. Description of the Prior Art:

Parasitic mites cause damages to plants such as citrus fruits, apple tree, tea, cotton, cedar, rose, carnation and other various trees, vegetables, ornamental plants and to animals and the others. It is trouble to control the mites because an average life of mites is about 20 days and developments of mites for ten and several times per year have been found.

In the development of mites, larvae and ova of mites are included. Accordingly, it has been required to find a miticidal compound which has imagocidal, larvacidal and ovumcidal effects for a long period.

SUMMARY OF THE INVENTION

It is an object of the present invention to provide a miticidal method for controlling mites.

Another object of the present invention is to provide a miticidal method for inhibiting a development of mites.

These objects of the present invention has been attained by applying Salinomycin or a derivative thereof to mites.

DETAILED DESCRIPTION OF THE PREFERRED EMBODIMENTS

Salinomycin can be successfully isolated from a fungus body and medium, which is cultured from a Salinomycin producing Streptomyces alpse microorganism, Streptomyces albus 80,614 (Fermentation Research Institute of the Agency of Industrial Science and Technology of Japan No. 419) ATCC 21,838.

Isolation of Salinomycin can be accomplished extracting it from the cultured medium with an organic solvent such as butyl acetate, acetone, chloroform, etc. and concentrating the extract under a reduced pressure and then treating the product with a column chromatography.

The Salinomycin has the following formula in acid form. The acid group can be converted to suitable salts or amides by the conventional method. Hereinafter, the Salinomycin and the salts and amides thereof are referred as Salinomycins.

The typical salts include sodium, potassium, calcium, magnesium and ammonium salts. Heavy metal salts of Salinomycin can be used if an environmental pollution is not caused. The typical amides includes dimethyl, diethyl, dipropyl, dubutyl amides.

The inventors have studied the applications of Salinomycins and have found that Salinomycins have strong miticidal effect to control imago, larva and ovum of mites.

The Salinomycins are effective for controlling various types of plant and animal parasitic mites including spider mites such as citrus red mite, European red mite, Kanzawa spider mite, two-spotted spider mite, carmine mite, sweet cherry spider mite, clover mite, Sugi spider mite, sourthern red mite, Smith spider mite, and rust mite, red mite, root mite, and house mite, rickettsia orientalis, hair mite, powder mite and dust mite, etc..

The miticidal compositions of Salinomycins with suitable carrier can be applied in the form of emulsion, granules, powder, wettable powder, aerosol, etc.. The carriers include clay, diatomaceous earth, talc, silica gel, bentonite, water organic solvent, air, freon etc.. It is possible to add suitable additives such as a spreader, an emulsifier, a dispersing agent, a wetting agent, etc..

The miticidal compositions of Salinomycins can be used by admixing with the other ingredient such as a fertilizer, and the other agricultural chemicals e.g. other miticidal compounds of organic phosphates, thiophosphates and thiazolyl esters, external preparations for animals, repellents, etc..

The miticidal compositions of Salinomycins are applied by a soil treatment, a foliar application, a spray application in animal cages and fowls, cages, and a coating, etc. at suitable ages of larvae, ova and imagines of mites depending upon the purpose of the application.

Suitable amount of the active ingredient of Salinomycins (as acid form) is dependent upon the object mites and is usually in a range of 1 to 50 ppm for controlling the animal parasitic mites and in a range of 10 to 200 g per 10 ares for controlling the plant parasitic mites.

Salinomycin is usually applied in an amount ranging 1 to 1,000 mg/m$^2$ preferably 10 to 200 mg/m$^2$.

The Salinomycins can exhibit remarkable miticidal effect as shown in the following experiments.

The Salinomycins are usually applied as the miticidal compositions. Typical examples of miticidal compositions are illustrated.

COMPOSITION 1

A 10 wt. parts of sodium salt of Salinomycin was dissolved in a mixture of 35 wt. parts of xylene and 35 wt. parts of dimethyl formamide, and 5 wt. parts of alkylaryl polyoxyethylene was added to the solution to form an emulsifiable concentrate and the emulsifiable concentrate was diluted with water to spray it.

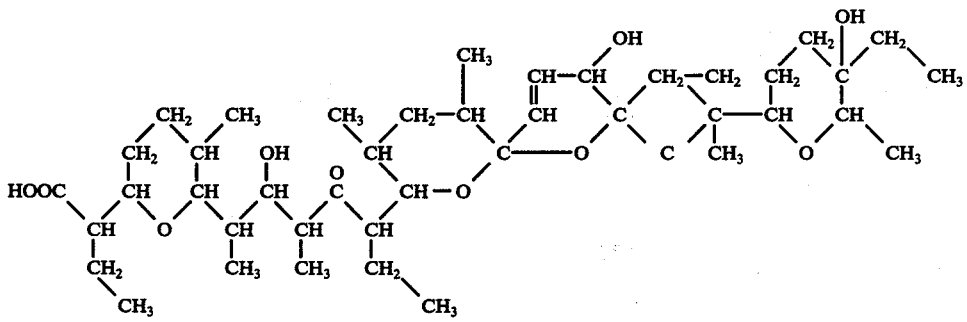

COMPOSITION 2

A 0.1 wt. part of sodium salt of Salinomycin, 5 wt. parts of silica gel, 60 wt. parts of clay, and 34.9 wt. parts of talc were crushed and mixed to form a powder.

COMPOSITION 3

A 10 wt. parts of sodium salt of Salinomycin, 15 wt. parts of silica gel, 40 wt. parts of clay, 30 wt. parts of diatomaceous earth and 5 wt. parts of a wet spreader (mixture of alkylbenzenesulfonate and ligninsulfonate 2 : 1 ) were mixed to form a wettable powder, and the wettable powder was diluted with water to spray it.

EXPERIMENT 1

EFFECT ON IMAGO OF MITES

Kidney bean seedlings were cultured and Kanzawa spider mites (imagines) were placed on cotyledons at a ratio of 20 per one group. The emulsifiable concentrate of Composition 1 was diluted with water to give the concentrations of Salinomycin stated in Table 1. The emulsions were respectively sprayed to the colyledons. After the treatment, the kidney bean seedlings were kept at 25° C for 24 hours in a room and the miticidal effects were tested. The results are shown in Table 1.

Table 1

| Active ingredient | Concentration of active ingredient (ppm) | Miticidal effect (%) (mortality) |
| --- | --- | --- |
| none | — | 0 |
| Salinomycin | 1000 | 100 |
| Salinomycin | 100 | 95 |

EXPERIMENT 2

EFFECT ON OVUM OF MITES

Kidney bean seedlings were cultured and Kanzawa spider mites (imagines) were placed on colyledons at a ratio of 10 per one group. After the ovipositions of mites for one day and night, the imagines were removed. The emulsion prepared by diluting the emulsifiable concentrate of Composition 1 was sprayed. After the treatment, the colyledons were kept at 25° C for 6 days in a room and the unhatchabilities were tested. The results are shown in Table 2.

Table 2

| Active ingredient | Concentration of active ingredient (ppm) | Number of ova | Unhatchability (%) (mortality) |
| --- | --- | --- | --- |
| none | — | 131 | 0 |
| Salinomycin | 1000 | 122 | 90.5 |
| Salinomycin | 100 | 117 | 52.3 |

EXPERIMENT 3

EFFECT ON LARVA OF MITES

In accordance with the process of Experiment 2, the oviposition of Kanzawa spider mites were resulted on colyledons of kidney bean seedlings. The emulsion prepared by diluting the emulsifiable concentrate of Composition 1 was sprayed to larvae of mites. After the treatment, the colyledons were kept at 25° C for 24 hours in a room and miticidal effects were tested. The results are shown in Table 3.

Table 3

| Active ingredient | Concentration of active ingredient (ppm) | larvae miticidal effect (%) (mortality) |
| --- | --- | --- |
| none | — | 0 |
| Salinomycin | 1000 | 100 |
| Salinomycin | 100 | 100 |
| Salinomycin | 50 | 100 |

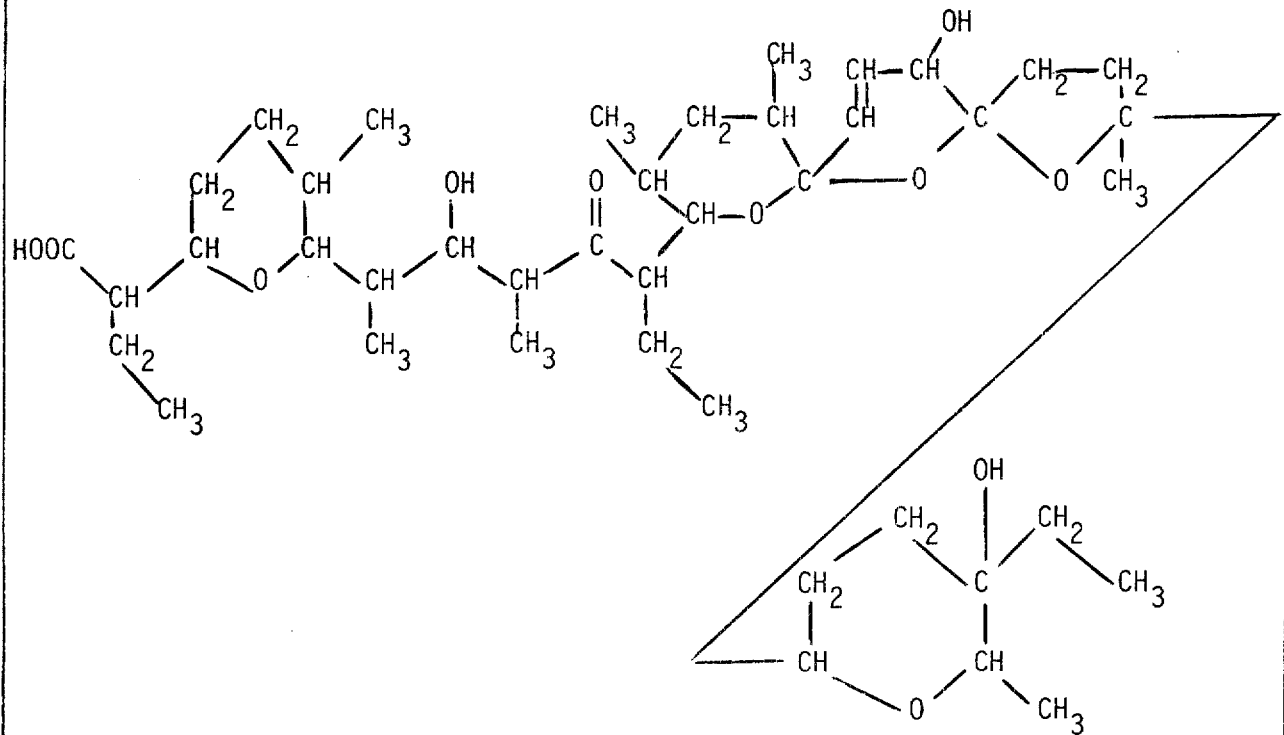

What is claimed is:

1. A method for destroying mites which comprises applying a composition comprising a miticidally effective amount of Salinomycin in combination with a carrier therefor, to imagines, larvae or ova of mites.

2. A miticidal method according to claim 1, wherein Salinomycin is applied in an amount ranging 1 to 1,000 mg/m$^2$.

3. A miticidal method according to claim 1, wherein Salinomycin is applied as an external preparation for animals.

* * * * *

UNITED STATES PATENT OFFICE
CERTIFICATE OF CORRECTION

Patent No. 4,066,781        Dated January 3, 1978

Inventor(s) Hajime Shibuya et al.

It is certified that error appears in the above-identified patent and that said Letters Patent are hereby corrected as shown below:

Column 1, line 54, delete "dubutyl" and insert therefor -- dibutyl --.

Column 1, the bottom, delete present formula and insert therefor --

Signed and Sealed this

Twenty-ninth Day of August 1978

[SEAL]

*Attest:*

RUTH C. MASON
*Attesting Officer*

DONALD W. BANNER
*Commissioner of Patents and Trademarks*

UNITED STATES PATENT OFFICE
CERTIFICATE OF CORRECTION

Patent No. 4,066,781  Dated January 3, 1978

Inventor(s) Hajime Shibuya et al.

It is certified that error appears in the above-identified patent and that said Letters Patent are hereby corrected as shown below: